US010332174B2

(12) United States Patent
Hubman

(10) Patent No.: US 10,332,174 B2
(45) Date of Patent: Jun. 25, 2019

(54) PROCESS FOR PREPARATION AND PURCHASE OF INDIVIDUALIZED COSMETICS UNDER A PRINCIPAL BRAND AND DEVICE ACCORDING TO THE SAID PROCESS

(71) Applicant: VASTOK D.O.O., Ljubljana (SI)

(72) Inventor: Danijel Hubman, Litija (SI)

(73) Assignee: VASTOK D.O.O., Ljubljana (SI)

( * ) Notice: Subject to any disclaimer, the term of this patent is extended or adjusted under 35 U.S.C. 154(b) by 394 days.

(21) Appl. No.: 15/109,073

(22) PCT Filed: Dec. 30, 2014

(86) PCT No.: PCT/SI2014/000088
§ 371 (c)(1),
(2) Date: Jun. 29, 2016

(87) PCT Pub. No.: WO2015/102543
PCT Pub. Date: Jul. 9, 2015

(65) Prior Publication Data
US 2016/0328772 A1  Nov. 10, 2016

(30) Foreign Application Priority Data

Dec. 31, 2013  (SI) .................................. 201300455

(51) Int. Cl.
*G06Q 30/00* (2012.01)
*G06Q 30/06* (2012.01)
(Continued)

(52) U.S. Cl.
CPC ..... *G06Q 30/0621* (2013.01); *G06Q 30/0222* (2013.01); *G06Q 30/06* (2013.01);
(Continued)

(58) Field of Classification Search
None
See application file for complete search history.

(56) References Cited

U.S. PATENT DOCUMENTS 5,622,692 A * 4/1997 Rigg ...................... A61B 5/442
356/402
6,516,245 B1 * 2/2003 Dirksing ................ A45D 40/00
700/233
(Continued)

FOREIGN PATENT DOCUMENTS

| JP | 2002073944 | 3/2002 |
| KR | 20100062903 | 6/2010 |
| WO | WO 0191601 | 12/2001 |

*Primary Examiner* — Mila Airapetian
(74) *Attorney, Agent, or Firm* — Gina M. Lupino

(57) ABSTRACT

The present invention belongs to the field of systemized preparation and sale of individualized cosmetics, more precisely it belongs to the field of systems, devices and processes for creation of own cosmetic products and the sale method of said products.

Figure 1:
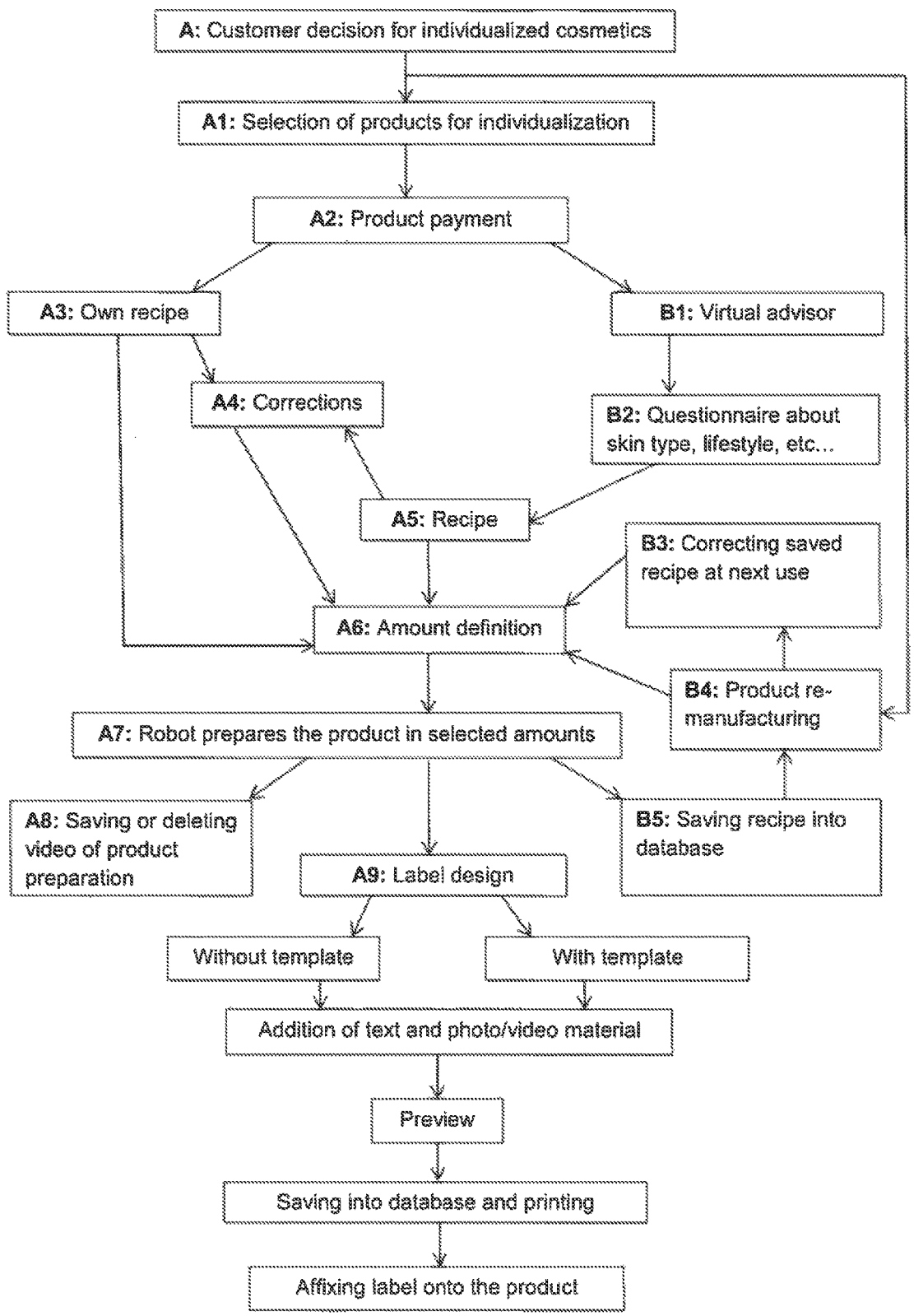

The essence of the process for preparation and purchase of individualized cosmetics under a principal brand is that the process is a part of a device, which performs this process, and that the process includes the following steps: entering into the shop, beginning of video recording and/or photographing, selecting a product for purchase, creating customer profile, whereby the customer receives his own code, payment, decision for an individual recipe or activation of virtual advisor, creation of individual recipe, or recipe review, selection of options for changing the recipe, storage of recipe under a new sub-brand, which includes the principal brand on the first place, possibility to alter the new recipe, enabling availability of the recipe for others, beginning of product making, product closing, printing product information and product labelling, purchase entry to the customer's code, entry of customer's bonuses, and product (Continued)

shipping. The process allows the possibility of active participation in creation of own recipes and sub-brands, which can be closed for others or can be offered to other customers, which means that the creator can participate in the rewarding scheme depending on the number of sold products.

20 Claims, 2 Drawing Sheets

(51) Int. Cl.
    *G06Q 30/02*     (2012.01)
    *G06Q 50/00*     (2012.01)
    *H04N 5/77*     (2006.01)
    *A61K 8/00*     (2006.01)

(52) U.S. Cl.
    CPC ............. *G06Q 50/01* (2013.01); *H04N 5/772* (2013.01); *A61K 8/00* (2013.01); *A61K 2800/10* (2013.01); *A61K 2800/805* (2013.01)

(56) References Cited

U.S. PATENT DOCUMENTS

| | | | |
|---|---|---|---|
| 8,967,851 B1* | 3/2015 | Kemeny | B01F 7/00908 366/142 |
| 2005/0021174 A1 | 1/2005 | Wilmott et al. | |
| 2005/0211768 A1* | 9/2005 | Stillman | G07F 11/00 235/381 |
| 2006/0124196 A1* | 6/2006 | Bartholomew | G07F 11/165 141/100 |
| 2009/0076639 A1 | 3/2009 | Pak | |
| 2013/0084259 A1 | 4/2013 | Lee | |
| 2013/0310955 A1* | 11/2013 | Minvielle | G06F 16/24 700/28 |
| 2015/0021356 A1* | 1/2015 | Witchell | G01F 1/42 222/23 |

* cited by examiner

PROCESS FOR PREPARATION AND PURCHASE OF INDIVIDUALIZED COSMETICS UNDER A PRINCIPAL BRAND AND DEVICE ACCORDING TO THE SAID PROCESS

FIELD OF INVENTION

This invention relates to the systemized preparation and sale of individualized cosmetics, more precisely to systems, devices and processes for the creation of individualized cosmetic products and the sale method of these products.

SUMMARY OF INVENTION

The system, devices, and processes are used to design and prepare individualized, customized cosmetics and their respective branding according to predetermined instructions or a user's instructions. The system, devices, and processes prepare cosmetics using basic recipes under a principal brand, as well as customizable, individualized cosmetics under sub-brands of the principal brand. The system may include individual recipes under the sub-brands. The system is used to promote and sell the principal and sub-brand products. The system also facilitates ordering of the cosmetic products, labelling, payment, and shipping to the customer.

The system, devices, and processes enable the creation of cosmetic products and customizing them based on product composition and product labelling. The system has a database containing basic product recipes, and a computer program and an interactive interference that allows a user to interact with the products in the database. The system may be implemented into a portable device (e.g. kiosk) or online.

The system and process provides options for the user (e.g. customer) who wishes to create custom, individual recipes under a sub-brand during an initial cosmetics purchase, alter the recipe during subsequent purchases, prevent others from accessing to the custom recipe, and permitting others to order or buy a the custom, individual cosmetic products under their sub-brand. The system and process also allows the user to market the custom cosmetic products and rewarding of customers for selling their product.

BACKGROUND

There are several different systems and methods that are used to prepare cosmetic products in a shop or online according to a customer's wishes and needs JP2002073944 describes a marketing method that-connects a customer to a producer's server and allows the customer to provide information needed to make individualized cosmetics. In this way a relationship between customers and producers can be built. In addition, this process also improves control and management of production, supplies and customer information.

US2013084259 describes a method for production of individualized cosmetics where the customer selects ingredients of the cosmetic product according to his/her own wishes and skin characteristics.

KR20100062903 describes a method for cosmetics individualization, where the customer connects with a server, enters data about skin characteristics and personal information, and ingredients are selected for a cosmetic product according to customer's wishes, based on the data entered by the customer.

US2009076639 describes a method and system for cosmetics individualization based on skin or hair characteristics, wherein a microprocessor contains a database with information for standard mixing ratios depending on age and skin or hair characteristics.

US2005021174 describes a system for the selection and production of an individualized cosmetics product, either implemented on the internet or in an autonomous unit, such as a kiosk. The recipe for the cosmetic product is made based on customer's wishes and other external factors. The recipe is then sent to production. At the same time the customer receives the recipe for the created individualized cosmetic product.

However the documents above do not disclose methods of marketing of created products and creation of sub-brands under one principal brand, or a rewarding system, which would enable a person with a successful individualized product to gain benefits at the principal brand.

DETAILED DESCRIPTION

In an embodiment, the process for preparation and purchase of individualized cosmetics under a principal brand is a part of a device, which executes this process. The process includes the following steps:
  entering a shop,
  beginning video recording and/or photographing,
  selecting a product for purchase,
  creating customer profile, whereby the customer receives his/her own code,
  payment,
  decision for an individual recipe or
  activation of virtual advisor,
  creation of individual recipe,
  or recipe review,
  selection of options for changing the recipe,
  storage of recipe under a new sub-brand, which includes the principal brand,
  altering the new recipe if desired,
  enabling availability of the recipe for others,
  beginning of product making,
  product closing,
  printing product information and product labelling,
  purchase entry to the customer's code,
  entry of customer's bonuses, and
  product shipping.

In addition to creating own recipes and own sub-brands, in an embodiment, the process allows for active participation in the creation of recipes and sub-brands. The recipes can be kept secret from or unavailable to (i.e. from other customers) or alternatively available and offered to other customers. In an embodiment, the creator can participate in the rewarding scheme depending on the number of sold products.

An embodiment of the process for preparation and purchase of individualized cosmetics under a principal brand is described in FIGS. 1 and 2 below.

Figure 2:
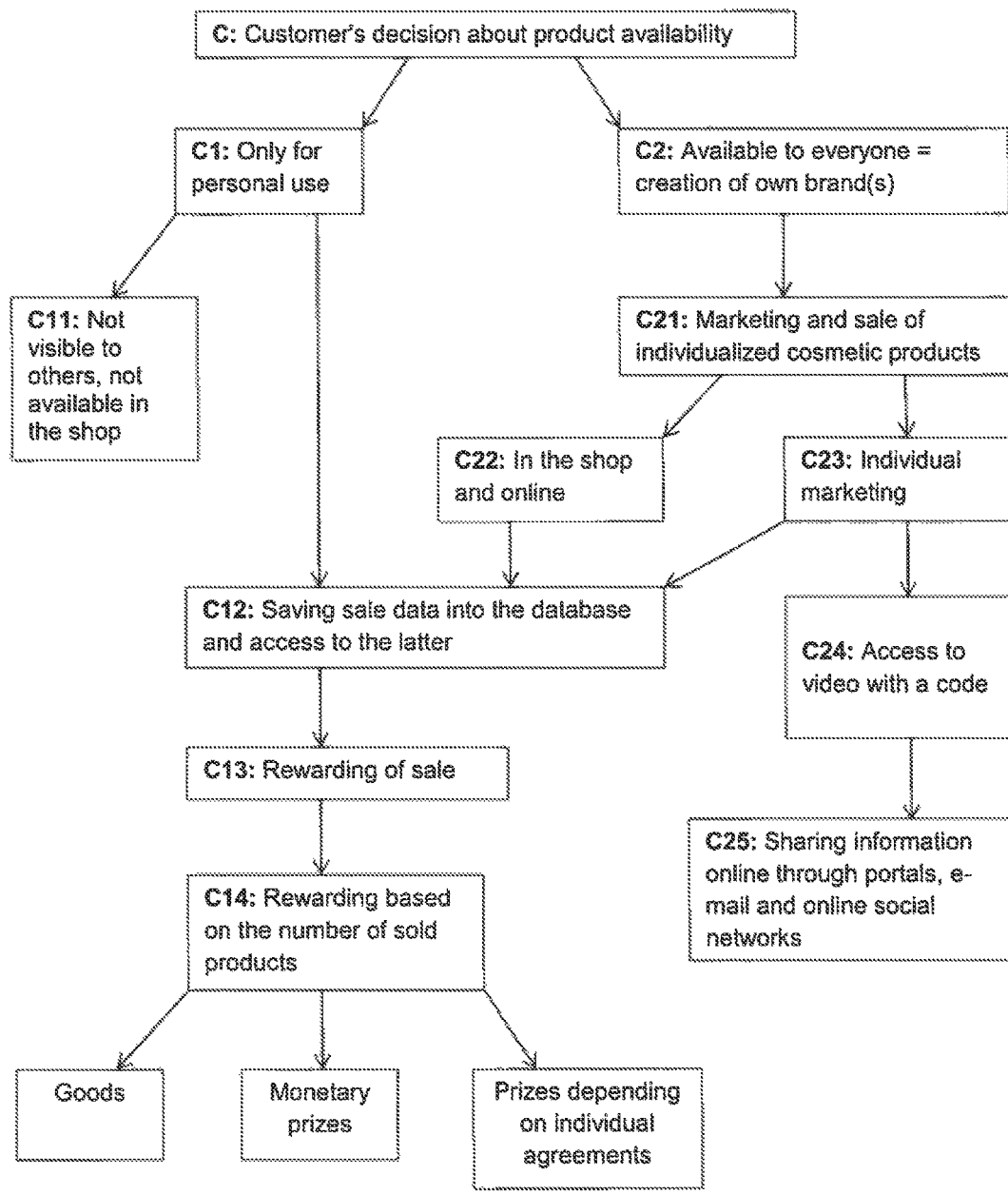

FIG. 1 Block diagram of the process for preparation of an individualized cosmetic product in a shop and/or on the internet FIG. 2 Block diagram of individualized cosmetic product marketing FIGS. 1 and 2 illustrate an embodiment of a system and process for preparation and purchase of individualized cosmetics products under a principal brand. The system and process may be performed at any convenient location, such as a shop, an exhibition area or a manufacturing-warehouse space reserved for organized processing and preparation of internet orders of cosmetic products. In an embodiment, the system has an automated machine or robot, which prepares the cosmetic products, such as cream, soap, shampoo, body milk and similar, according to customer's wishes and/or needs. Cosmetics products may be prepared on-site in a shop or an exhibition area or remotely, from a distance away from a shop over the internet. In an embodiment where the cosmetics are prepared on-site, the customer may receive a lab coat and the system may record the whole cosmetic product creation process. Product purchase will be done in the shop before the beginning of product production.

Referring to FIGS. 1 and 2, in an embodiment, the system allows the customer to create and sell his/her own cosmetic products under a principal brand, buy them, and/or allow other customers to buy them, and receive rewards (e.g. sales milestones) for the sub-brand products sold under the principal brand.

In an embodiment, the system for preparation and purchase of individualized cosmetics under a principal brand operates as follows and the process for the preparation and purchase of individualized cosmetics under the principal brand includes the following steps:

Step A: The system invites the customer to confirm the decision to prepare and purchase an individualized cosmetic product. The customer confirms the decision to prepare and purchase an individualized cosmetic product.

Step A1: The system invites the customer creates his/her profile, obtains his/her code, and selects a product. The customer creates his/her profile, obtains his/her code, and selects a product.

Step A2: The system invites the customer to select a product from a range of possible products, provide payment, and proceed to step A3 or B1. The customer selects the desired product (e.g. facial cream, hand cream, lip balm, shampoo, body milk, etc.), provides payment, and selects step A3 or step B1

Step A3: The system invites the customer to prepare the selected product by selecting ingredients for the product (the "Initial Recipe Data"). The customer and selects ranges and combinations of ingredients for the product. The system has predetermined ranges and combinations of ingredients that are compatible with one another. The system allows the customer to select ingredients based on these predetermined ranges and combinations.

Step B1: The virtual advisor prepares proposed amounts of ingredients that are in accordance with regulations.

Step A4: The system invites the customer to amend the recipe (e.g. ratios and number of ingredients) ("Amended Recipe Data") if desired and submit it for production. The customer may accept the recipe, or alternatively amend it and then accept the amended recipe.

Step B2 (Optional): The system has a virtual advisor available to assist the customer throughout the process. If the customer selects step B2, a virtual advisor will request data about the customer's age, skin type, and lifestyle, and propose a range of amounts for each ingredient of the product based on this data. The customer may change the ingredient amount in the proposed range, select or change the amounts of ingredients in a cosmetic product overall, and/or accept the proposal of the virtual advisor. After completing Step B2, the system sends the acquired data (i.e. age, skin type, lifestyle) to step A5

Step A5: The system gathers all ratios of ingredients, saves the recipe, and sends it to step A6. The customer confirms and authorizes the system to enter the recipe for production.

Step A6: The system gathers all data regarding the selected or created recipe from steps A3 and/or A4, namely the Initial Recipe Data and Amended Recipe Data, and saves it. The system also invites the customer to choose the final amount of the cosmetic product (e.g. tester, small, medium, large sizes). The system then sends the data to a robot A7.

Robot A7 receives data and information from the system and creates the cosmetic product based on the data received from the system. For container selection, all ingredients will be dosed, closed and mixed, based on the valid recipe and selected dose size. Robot A7 may have an integrated camera in order to record and save the process of making a product. Robot A7 may be a computer controlled machine that enables execution of the whole process.

The system allows the customer to design custom labels for the products. When mixing is done, the system prepares the product for labelling. The label may include the principal brand and images or other contents from base A8 or other available databases, including USB keys and/or computer disc, if the customer is performing the process on the internet. Step A9 contains tools for design and production of labels, which can be made with or without a template.

The system saves all data regarding the custom designed cosmetic products in a database. From step B3 it is possible to correct a saved recipe in step A5 if it is selected again, from base B4 is possible to search recipes in step A5, and through step B5 save the corrected recipe as a new recipe in the database. This allows saving created recipes for a product in the database, from which it is possible to re-prepare the cosmetic product and to fill the packaging, as well as to the correct recipes for individualized cosmetic products. Step A9 allows the customer to individually design the label with or without a template, wherein the customer can add his/her sub-brand in addition to the principal brand. The label may also include images, which have been taken during product making or from a webcam if the process is performed online or from different media for data storage. The customer can also add text, which may be limited to a certain number of characters (e.g. 140 characters including spaces, appropriate for Twitter posts), that describe the product, process for making the product and/or its author, etc. In an embodiment, the system is configured to prevent the customer from adding text containing offensive elements or other brands. In an embodiment, the pre-prepared label contains all elements required by the law, such as expiry date, product ingredients, and sign of the principal brand and similar. The system is configured to allow the customer to preview and amend the label and before printing the label. When the customer is satisfied with the label, a command for label printing and affixing is triggered. Step A9 can be done between steps A6 and A7. From step A it is also possible to choose entry into step B4, when the customer has an already saved recipe in step A5.

Product payment is done after the receipt of product, if the process is performed in a classic shop or if it is not performed online.

In an embodiment, the system is configured to allow a customer to create an individualized cosmetic product under a principal brand as follows:

1. the customer selects the required product (for example cream, shampoo, body milk . . . );
2. the product composition is determined based on age, skin type and other parameters, such as preferred scent, lifestyle and similar;
3. the virtual advisor prepares proposed amounts of ingredients, in accordance with regulations, and the amounts are proposed for each component as a range, within which the customer is able to alter the amount. The customer may choose between the proposal of the virtual advisor and individual alteration of ingredient amounts;
4. the desired amount of the cosmetic product selected, wherein several possibilities such as tester, small dose, large dose, family dose, are available;
5. the virtual advisor triggers the process for preparation of the individualized cosmetic product, which is performed by the robot;
6. the robot selects the appropriate container for cosmetic product preparation;
7. the product recipe is saved into the database, from which it is possible to re-prepare this product as well as to correct the recipe for the individualized cosmetic product;
8. product labelling with labels, which are prepared with or without templates, wherein:
   a. the customer may create the label individually, and insert images, which have been taken during product making or from a webcam if the process is performed online or from different media for data storage;
   b. the customer may also add text, which is limited with the number of characters appropriate for Twitter posts (140 characters including spaces), that describe the product, process for making the product and/or its author, wherein the text does not contain offensive elements or other brands;
   c. the label contains all elements required by the law, such as expiry date, product ingredients, and sign of the principal brand and similar;
   d. preview of the label and possible corrections are allowed before label printing;
   e. the label is printed; and
   f. the label is affixed onto the cosmetic product.

In an embodiment, the is performed so that the customer in the third point of the above paragraph defines the cosmetic product composition on his/her own without the help of the virtual advisor, but in accordance with regulations, wherein the software does not allow mixing components, which could interact with each other and could be toxic. At the same time the components are limited in amount ranges, which are weight or volume percentages.

Receipt of the individualized product depends on the site of preparation. In an embodiment where the process is performed in a shop or exhibition area, the product is claimed on site. In an embodiment where the product is prepared online, the delivery options are chosen with the help of the application, wherein the delivery may be by mail or personal delivery, the location is selected for the latter option.

FIG. 2 shows block scheme for marketing and sale acceleration of prepared individualized cosmetic products as well as rewarding of customers, who have created individualized cosmetic products.

After the process of cosmetic product creation is complete the creator/customer decides in step C about the final product availability as shown in FIG. 2. Step C has two options, step C1 and step C2. Step C1 includes option C11, in which the recipe is locked, cannot be seen by others and the products are not available in the shop. The other option of step C1 is C12, which includes saving into the database of sold products and access to the customer to review sold products. Depending on the number of sold products, which is recorded in C12, the number of points for rewards is computed in C13 and with respect to customer's selection in step (C14) divides then to prizes in goods, monetary prizes and/or prizes according to the agreement.

From step C the customer can choose step C2, which enables all following and/or new customers access to the created product, and that in step C21 the individualized product is presented and offered. From step 21 active presentation and sale of the product is done in step C22, which is a shop or an online store. From step C22 data about sales are recorded in step C12, in which the customers have access to database and sale information. From C12 data are transferred to C13, in which obtained points are evaluated as the basis for rewarding. From step C21 it is possible to continue to step C23, which is individual marketing. From step C23 data are transferred to C12, which includes access to database and/or saved video protected with a code, and leads to step C25. Step C25 allows sharing information on the internet through portals, e-mail and social networks.

In an embodiment, the system is configured to allow the customer to:
Make the product available to all, and:
   create a new brand with an additional recognition element added to the principal brand, which will allow separating of products based on their creators;
   allow marketing and sales promotion to be done by representatives of the principal brand in shop, online or in other media, so that in the shop best selling or newest individualized products created by customers are offered next to products under the principal brand. New customers will have the option to buy already prepared products or products created by other customers or to create a new individualized product;
   advertise individualized products by sharing information through internet portals, social networks, e-mail and other channels, and making the video, which was recorded during individualized product preparation, available to creators;
Make the product private, for personal use, and not available to others in shops, online stores or other sale channels;
receive awards; regardless of product availability the customer receives a code after creating his/her individualized product, by which he/she gains access to applications that allow access to information about sold products under their sub-brand;
stimulate marketing by rewarding, based on the number of sold products, wherein the prizes can be goods, monetary prizes or can depend on individual agreements.

The disclosed system and process for preparation and purchase of individualized cosmetics under a principal brand allows classic product selection with the offered recipe, creating own recipes and sub-brands, the decision to actively participate in creating own recipes and sub-brands that can be closed for others or can be offered to other customers, as well as participation in the rewarding scheme depending on the number of products sold. The described process is a part of the device, which is configured to allows the customer to access the system or shop and select products, create ingredient ratios for a defined product, and receive an actual cosmetic product.

The invention claimed is:
1. A process for the preparation and purchase of individualized cosmetics under a principal brand, the process comprising:

creating a profile based on the input data, obtaining a code, and selecting a product type from a predetermined range of product types;
providing payment;
selecting preparation of previously selected product;
selecting ingredient characteristics associated with the product;
adjusting the selected ingredient characteristics to form a recipe;
creating recipe data associated with the recipe based on the selected ingredient characteristics;
transferring the recipe data to a robot;
activating a camera inside the robot to film the method of making the product;
storing the filmed method in the profile;
selecting a container based on the recipe data;
obtaining, measuring, and mixing the ingredients in the container based on the recipe data;
preparation of a label including the principal brand; and
delivering the product to the customer.

2. The process of claim 1, further comprising:
a virtual advisor proposing amounts of ingredients for preparation of the selected product;
querying the customer with questions about the customer's skin type and lifestyle;
receiving the customer's answers to the questions;
amending the recipe based on the customer's answers;
saving the amended recipe into the database as a new recipe; and
transferring the recipe to a robot for selecting a container and mixing and sealing all ingredients in the container.

3. The process of claim 1, wherein the step of preparing the label comprises preparing a custom label using a template, not using a template, or adding a sub-brand.

4. The process of claim 1, wherein the label comprises images, text, or a combination thereof.

5. The process of claim 1, further comprising locking the recipe such that the product is not available in the shop.

6. The process of claim 1, further comprising:
saving into the database product sales data comprising the number of products sold by the customer to third parties;
computing a number of points based on the product sales data; and
sending prizes to the customer based on the product sales data.

7. The process of claim 1, further comprising locking the recipe such that it cannot be seen by others.

8. The process of claim 6, wherein the customer may optionally allow other customers to access and purchase the final product, and the customer earns points based on the other customer sales.

9. The process of claim 1, further comprising marketing the product saved video on the internet through portals, e-mails and social networks.

10. The process for preparation and purchase of individualized cosmetics under principal brand according to claim 1, further comprising providing payment after receipt of the product or on the internet.

11. A process for the preparation and purchase of an individualized cosmetic product under a principal brand, the process comprising providing a system comprising
a input terminal comprising user interface configured to acquire input data associated with the user from the user,
a database for storing the user input data, a group of predetermined cosmetic product options, and a group of predetermined recipes,
volumes of ingredients for the cosmetic product;
a robot for preparing and mixing the cosmetic product option based on the input data; and
an actuator for actuating the robot;
a printer for printing a label for the product;
providing the input data to the system via the user interface for the cosmetic product by selecting a cosmetic product from the group predetermined cosmetic product options;
creating a user profile in the system based on the input data;
providing payment data to the system for the selected cosmetic product via the user interface;
storing the payment data to the system;
providing a recipe to the system for the selected cosmetic product under a sub-brand;
preparing the selected cosmetic product based on the input data and the recipe;
creating a product label based on the input data and the sub-brand;
actuating the robot to prepare the cosmetic product based on the user input and the recipe;
printing the product label comprising the sub-brand;
affixing the product label onto the product;
delivering the product to the user; and
determining an award for the user based on the stored payment data;
associating the award with the user profile;
notifying the user of the award.

12. The process of claim 11, wherein the user input terminal comprises a computer, a kiosk, or a combination thereof.

13. The process of claim 11, wherein the system further comprises a points tallying system.

14. The process of claim 11, wherein the system further comprises a virtual advisor for assisting the user with providing the recipe for the selected cosmetic product.

15. The process of claim 11, wherein the step of providing a recipe for the selected cosmetic product under a sub-brand comprises
creating a new recipe or selecting a recipe from the group of predetermined recipes;
reviewing the recipe;
optionally amending the recipe; and
storing the amended recipe under the sub-brand.

16. The process of claim 11, wherein the system further comprises a camera.

17. The process of claim 16, further comprising activating the camera and recording product preparation.

18. The process of claim 11, further comprising adding the recipe to the group of predetermined recipes for use by other users.

19. The process of claim 11, further comprising storing the recipe in the system in the user profile for use only by the user.

20. The process of claim 11, further comprising marketing the product to third parties under the sub-brand.

* * * * *